(12) United States Patent
Yabukami et al.

(10) Patent No.: US 8,729,284 B2
(45) Date of Patent: May 20, 2014

(54) PROCESS FOR PRODUCTION OF MESO-FORM AND RACEMIC FORM METALLOCENE COMPLEXES

(75) Inventors: Minoru Yabukami, Ichihara (JP); Takuji Okamoto, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 13/992,082

(22) PCT Filed: Nov. 24, 2011

(86) PCT No.: PCT/JP2011/006525
§ 371 (c)(1),
(2), (4) Date: Aug. 27, 2013

(87) PCT Pub. No.: WO2012/077289
PCT Pub. Date: Jun. 14, 2012

(65) Prior Publication Data
US 2014/0031574 A1    Jan. 30, 2014

(30) Foreign Application Priority Data
Dec. 6, 2010  (JP) ................................ 2010-271428

(51) Int. Cl.
*C07F 17/00*   (2006.01)
*B01J 31/38*   (2006.01)
*C08F 4/72*    (2006.01)
*C07F 7/00*    (2006.01)
*C07F 7/08*    (2006.01)

(52) U.S. Cl.
CPC . *C07F 17/00* (2013.01); *C07F 7/00* (2013.01); *C07F 7/0801* (2013.01); *C07F 7/0807* (2013.01); *C08F 4/72* (2013.01); *B01J 31/38* (2013.01); *Y10S 526/943* (2013.01)
USPC .................. 556/11; 556/12; 556/53; 556/402; 556/431; 556/467; 526/170; 526/943; 502/103

(58) Field of Classification Search
CPC ........ C07F 7/0801; C07F 7/0807; C07F 7/00; C07F 17/00; C07F 19/00; C08F 4/72; B01J 31/38
USPC ........ 556/11, 12, 53, 402, 431, 467; 526/170, 526/943; 502/103
See application file for complete search history.

(56) References Cited

U.S. PATENT DOCUMENTS

| | | |
|---|---|---|
| 6,770,772 B2 | 8/2004 | Kashiwamura et al. |
| 6,906,155 B1 | 6/2005 | Minami et al. |
| 6,995,279 B2 | 2/2006 | Ushioda et al. |
| 7,173,099 B1 | 2/2007 | Minami |
| 7,199,202 B2 | 4/2007 | Minami et al. |
| 7,320,950 B2 | 1/2008 | Okamoto et al. |
| 7,544,758 B2 | 6/2009 | Minami et al. |
| 2003/0017940 A1 | 1/2003 | Kashiwamura et al. |
| 2004/0127731 A1 | 7/2004 | Ushioda et al. |
| 2005/0043495 A1 | 2/2005 | Minami et al. |
| 2006/0293471 A1 | 12/2006 | Minami et al. |
| 2007/0043192 A1 | 2/2007 | Okamoto et al. |
| 2009/0215973 A1 | 8/2009 | Minami et al. |

FOREIGN PATENT DOCUMENTS

| | | |
|---|---|---|
| JP | 7-505418 | 6/1995 |
| JP | 11-508596 | 7/1999 |
| JP | 11-508597 | 7/1999 |
| JP | 2000-95820 | 4/2000 |

(Continued)

OTHER PUBLICATIONS

International Preliminary Report on Patentability issued Jun. 20, 2013 in PCT/JP2011/006525 filed Nov. 24, 2011.

(Continued)

*Primary Examiner* — Porfirio Nazario Gonzalez
(74) *Attorney, Agent, or Firm* — Oblon, Spivak, McClelland, Maier & Neustadt, L.L.P.

(57) ABSTRACT

A method for producing an anionized meso-form double-cross-linked ligand represented by formula (3), including: bringing a compound represented by formula (1) into contact with a compound represented by formula (2) at −25° C. or less; and introducing an anionizing agent within 5 hours after the contact, wherein $R_1$ to $R_{10}$ are independently a hydrogen atom, a hydrocarbon group having 1 to 20 carbon atoms, or the like; A and A' are independently a cross-linking group containing an atom belonging to the $14^{th}$ group of the periodic table; M and M' are independently an atom belonging to the $1^{st}$ or the $2^{nd}$ group of the periodic table.

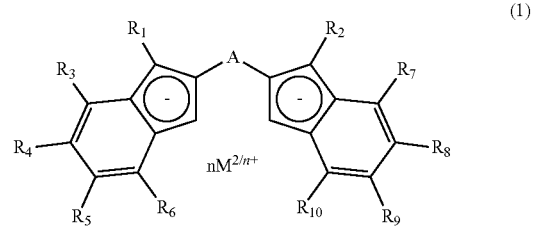

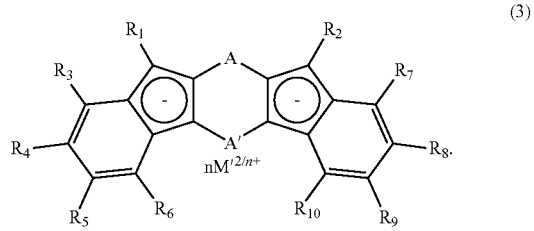

6 Claims, No Drawings

(56) References Cited

FOREIGN PATENT DOCUMENTS

| | | |
|---|---|---|
| JP | 2000-256411 | 9/2000 |
| JP | 2002-308893 | 10/2002 |
| JP | 2004-2310 | 1/2004 |
| JP | 2004-352707 | 12/2004 |
| JP | 2007-514684 | 6/2007 |
| WO | WO 97/03080 A1 | 1/1997 |
| WO | WO 97/03081 A1 | 1/1997 |
| WO | WO02/24714 A1 | 3/2002 |
| WO | WO 2005/058929 A1 | 6/2005 |

OTHER PUBLICATIONS

Written Opinion issued Dec. 27, 2011in PCT/JP2011/006525 filed Nov. 24, 2011.

International Search Report issued Dec. 27, 2011 in PCT/JP2011/006525.

Winfried Mengele, et al., "ansa-Metallocene Derivatives. 27. Chiral Zirconocene Complex with Two Dimethylsilylene Bridges[1]", Organometallics, vol. 12, No. 5, 1993, pp. 1931-1935.

Edwin G. Ijpeij, et al., "2-Lithioindenyllithium: An Easily Accessible Intermediate for the One-Pot Synthesis of Single—and Double—functionalised 2-Indene Derivatives", Synthesis, No. 9, 2006, pp. 1408-1414.

Luigi Resconi, et al., "Selectivity in Propene Polymerization with Metallocene Catalysts", Chemical Reviews, vol. 100, No. 4, 2000, pp. 1253-1345.

Helmut G. Alt, et al., "Effect of the Nature of Metallocene Complexes of Group IV Metals on Their Performance in Catalytic Ethylene and Propylene Polymerization", Chemical Reviews, vol. 100, No. 4, 2000, pp. 1205-1221.

Luigi Resconi, et al., "Diastereoselective Synthesis, Molecular Structure, and Solution Dynamics of meso-and rac-[Ethylenebis(4,7-dimethyl-$\eta^5$-1-indenyl)]zirconium Dichloride Isomers and Chain Transfer Reactions in Propene Polymerization with the rac Isomer", Organometallics, vol. 15, No. 23, 1996, pp. 5046-5059.

Gianluca Melillo, et al., "Branching Formation in the Ethylene Polymerization with Meso Ansa Metallocene-Based Catalysts", Macromolecules, vol. 35, No. 25, 2002, pp. 9256-9261.

Ronald L. Halterman, et al., "Synthesis and Structure of $C_2$-Symmertic, Doubly Bridged Bis(indenyl)titanium and—zirconium Dichlorides", Organometallics, vol. 16, No. 15, 1997, pp. 3333-3339.

Johann Hiermeier, et al., "Limiting the Relative Orientation of Bridged Cyclopentadienyl Anions. Mono—and Dianions Derived from 4,4,8,8-Tetramethyltetrahydro-4,8-disila-s—indacenes", Organometallics, vol. 10, No. 6, 1991, pp. 1787-1793.

Shigenobu Miyake, Synthesis, Molecular Structure, and Racemate-Meso Interconversion for rac-$(Me_2Si)_{2\{\eta}^5$-$C_5H$-3-$(CHMe_2)$-5-$Me\}_2MCL_2$(M = Ti and Zr), Organometallics, vol. 17, No. 25, 1998, pp. 5528-5533.

US 8,729,284 B2

PROCESS FOR PRODUCTION OF MESO-FORM AND RACEMIC FORM METALLOCENE COMPLEXES

TECHNICAL FIELD

The invention relates to a meso-form and racemic-form double-cross-linked complexes, and a method for producing these double-cross-linked metallocene complexes.

BACKGROUND ART

Various attempts have been made to obtain an olefin polymer of which the primary structure, the molecular weight or the like are controlled by changing variously the structure of a metallocene complex structure (Patent Documents 1 and 2, Non-Patent Documents 1 and 2). Of the structures of a metallocene complex, the effect of symmetry of a metallocene complex (racemic-form (C2 symmetric), meso-form (Cs symmetric) exerted on the polymerization performance is significantly large. Therefore, studies are made on the synthesis or evaluation of polymerization performance of a metallocene complex having symmetry (Non-Patent Documents 3 and 4).

However, in the case of mono-cross-linked metallocene complex, a mixture of a racemic body and a meso body is obtained when a complex is synthesized. Therefore, various industrially inadvantageous steps, such as separation by re-crystallization, use of specific raw materials, use of an auxiliary reagent in the presence of light or the like, are required (Patent Documents 3-5).

On the other hand, in the case of a double-cross-linked metallocene complex, it is expected to obtain a theoretically pure raceme or meso body, and hence, various studies have been made. For example, in Non-Patent Document 5, various ethylene-double-cross-linked metallocene complexes are obtained as a pure raceme body. However, since multi-stage reaction steps are required, the yield thereof is significantly small.

Patent Documents 6 and 7 each disclose a method for producing a double-cross-linked metallocene complex having a silicon atom-containing cross-linking group. Specific polymerization performance has been found. However, in the case of a double-cross-linked metallocene complex having a silicon atom-containing cross-linking group, in addition to an intended meso-form ligand, another symmetric ligand (racemic-form) may be mixed in as an isomer. Therefore, in order to obtain an intended symmetric double-cross-linked metallocene complex, steps become complicated since washing that needs a large amount of an organic solvent or re-crystallization is required. In addition, since there is a problem that the yield of the complex is significantly reduced, industrial production of the complex is not realistic.

Further, due to the above-mentioned problems, it was difficult to find new functions in olefin polymerization by variously changing the structure of the meso-form double-cross-linked metallocene complex.

In association with this problem, Non-Patent Documents 6 to 8 each report an isomerization reaction of a double-cross-linked complex having a silicon-containing group.

As mentioned above, although a method for producing selectively a meso-form of a double-cross-linked complex having a silicon-containing group as a cross link has been required, an effective method has not yet been found.

Further, as for a racemic-form, the racemic-form double-cross-linked metallocene complex which was reported in the past has a low yield. Therefore, when polyolefin is produced on the industrial basis, there is a defect that the cost of a catalyst was high. For example, Bercaws or the like synthesized a Cp-based racemic-form dimethylsilylene-double-cross-linked metallocene-complex. Since the double-cross-linked complex as a raw material is a mixture of a meso form and a racemic-form, the racemic-form is separated by washing. Therefore, the yield of the double-cross-linked complex is as small as about 30% (Non-Patent Document 9).

Brintzinger et al obtained a racemic-form double-cross-linked ligand and a racemic-form double-cross-linked metallocene complex by utilizing a racemization reaction which proceeds from a meso-form double-cross-linked ligand. However, racemization does not proceed completely, and since only about 20 to 40% of a meso-form double-cross-linked metallocene complex is mixed in, purification by re-crystallization is required in order to obtain a raceme complex. The final yield of the racemic-form double-cross-linked metallocene complex is significantly small (Non-Patent Document 8).

Patent Documents 8 and 9 each study a double-cross-linked metallocene complex having an indene skeleton. Unlike the above-mentioned example, although a double-cross-linked ligand of a highly-pure racemic-form containing no meso form is obtained, the yield thereof is as low as 30 to 40%. In these documents, a double-cross-linked ligand is produced by coupling Ind-SiMe$_2$Cl as a raw material. This reaction is a complex reaction which yields other product than intended products, and hence, the yield is thought to be small.

RELATED ART DOCUMENTS

Patent Documents

Patent Document 1: JP-A-2004-2310
Patent Document 2: JP-A-2004-352707
Patent Document 3: JP-T-2007-514684
Patent Document 4: JP-T-H11-508596
Patent Document 5: JP-T-H11-508597
Patent Document 6: JP-A-2000-95820
Patent Document 7: JP-A-2002-308893
Patent Document 8: JP-A-2000-256411
Patent Document 9: WO2002/024714

Non-Patent Documents

Non-Patent Document 1: Chem. Rev. 2000, 100, 1253-1345
Non-Patent Document 2: Chem. Rev. 2000, 100, 1205-1221
Non-Patent Document 3: Organometallics 1996, 15, 5046-5059
Non-Patent Document 4: Macromolecules 2002, 35, 9256-9261
Non-Patent Document 5: Organometallics 1997, 16, 3333-3339
Non-Patent Document 6: Organometallics 1993, 12, 1931-1935
Non-Patent Document 7: Organometallics 1991, 10, 1787-1793
Non-Patent Document 8: Synthesis 2006, No. 9, 1408-1414
Non-Patent Document 9: Organometallics 1998, 17, 5528-5533

SUMMARY OF THE INVENTION

An object of the invention is to provide a method for producing selectively a meso-form double-cross-linked ligand or a racemic-form double-cross-linked ligand.

An object of the invention is to provide a method for producing selectively a meso-form double-cross-linked complex or a racemic-form cross-linked metallocene complex.

According to the invention, the following method for producing a meso-form double-cross-linked ligand or the like is provided.

1. A method for producing an anionized meso-form double-cross-linked ligand represented by formula (3), comprising:

bringing a compound represented by formula (1) into contact with a compound represented by formula (2) at −25° C. or less; and introducing an anionizing agent within 5 hours after the contact:

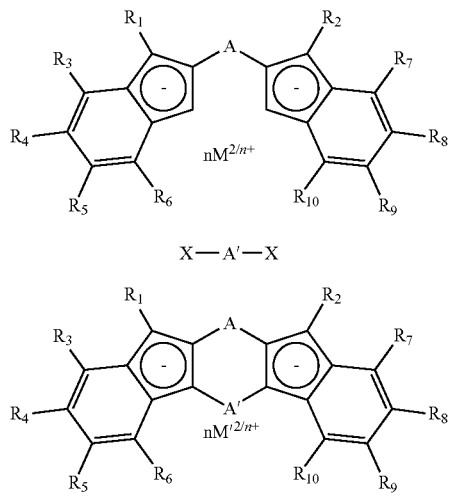

wherein $R_1$ to $R_{10}$ are independently a hydrogen atom, a hydrocarbon group having 1 to 20 carbon atoms, a silicon-containing group or a hetero-atom-containing group; A and A' are independently a cross-linking group containing an atom belonging to the $14^{th}$ group of the periodic table; M and M' are independently an atom belonging to the $1^{st}$ or the $2^{nd}$ group of the periodic table; n is 2 when M or M' is an atom belonging to the $1^{st}$ group of the periodic table, and 1 when M or M' is an atom belonging to the $2^{nd}$ group of the periodic table; and X is a halogen atom.

2. A method for producing an anionized racemic-form double-cross-linked ligand represented by formula (4), comprising:

bringing the compound represented by the formula (1) into contact with the compound represented by the formula (2) at 45° C. or higher, and introducing the anionizing agent 1 hour or more after the contact:

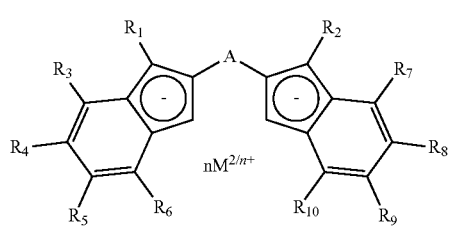

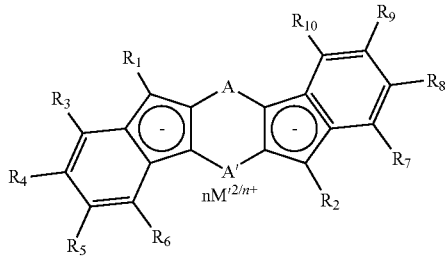

wherein $R_1$ to $R_{10}$ are independently a hydrogen atom, a hydrocarbon group having 1 to 20 carbon atoms, a silicon-containing group or a hetero-atom-containing group; A and A' are independently a cross-linking group containing an atom belonging to the $14^{th}$ group of the periodic table; M and M' are independently an atom belonging to the $1^{st}$ or the $2^{nd}$ group of the periodic table; n is 2 when M or M' is an atom belonging to the $1^{st}$ group of the periodic table, and 1 when M or M' is an atom belonging to the $2^{nd}$ group of the periodic table; and X is a halogen atom.

3. The production method according to 1 or 2, wherein A is dimethyl silylene or tetramethyl disilylene and A' is dimethyl silylene or tetramethyl disilylene.

4. A method for producing a double-cross-linked metallocene complex, comprising:

producing an anionized meso-form double-cross-linked ligand or an anionized racemic-form double-cross-linked ligand by the production method according to any of 1 to 3; and producing a double-cross-linked metallocene complex using the anionized meso-form double-cross-linked ligand or the anionized racemic-form double-cross-linked ligand.

According to the invention, it is possible to produce selectively meso-form double-cross-linked ligand or a racemic-form double-cross-linked ligand.

According to the invention, it is possible to produce selectively a meso-form double-cross-linked metallocene complex or a racemic-form double-cross-linked metallocene complex.

MODE FOR CARRYING OUT THE INVENTION

According to the first method of the invention, a compound represented by the formula (1) is brought into contact with the compound represented by the formula (2) at −25° C. or less. An anionization agent is introduced within 5 hours after the contact. According to the first production method of the invention, an anionized meso-form double-cross-linked ligand represented by the formula (3) can be obtained in a high yield (90% or more, for example).

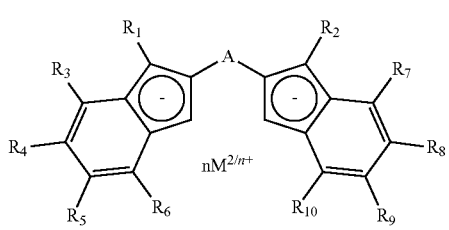

$$X-A'-X \quad (2)$$

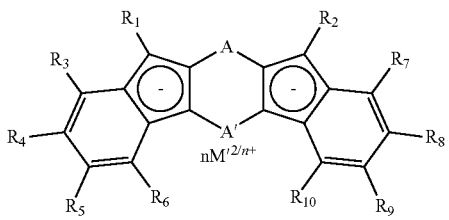

(3)

wherein $R_1$ to $R_{10}$ are independently a hydrogen atom, a hydrocarbon group having 1 to 20 carbon atoms, a silicon-containing group or a hetero-atom-containing group; A and A' are independently a cross-linking group containing an atom belonging to the $14^{th}$ group of the periodic table; M and M' are independently an atom belonging to the $1^{st}$ or the $2^{nd}$ group of the periodic table; and n is 2 when M or M' is an atom belonging to the $1^{st}$ group of the periodic table and 1 when M or M' is an atom belonging to the $2^{nd}$ group of the periodic table. X is a halogen atom.

In the formula (1) or (3), $R_3$ to $R_{10}$ may form a ring with adjacent groups.

The contact of the compounds represented by the formulas (1) and (2) is conducted at −25° C. or less. When conducting this reaction at a higher temperature, a meso-form double-cross-linked ligand formed by the contact may change to a racemic-form double-cross-linked ligand through an isomerization reaction. By suppressing the reaction temperature of this reaction to a low temperature, racemization reaction can be suppressed.

It is preferred that the temperature from the contact to the introduction of an anionization agent be retained at −25° C. or less.

In order to obtain a highly-pure meso-form double-cross-linked ligand, it is required to remove heat generation at the time of contact of the compound (1) and the compound (2) in order to keep low-temperature conditions. Therefore, a lower reaction contact temperature is preferable. Accordingly, the reaction temperature is preferably −30° C. or less, with −35° C. or less being more preferable. On the other hand, the cross-linkage forming reaction itself proceeds slowly when the temperature is too low. Therefore, the reaction temperature is preferably −50° C. or higher.

The mixing ratio (molar ratio) of the compound represented by the formula (1) and the compound represented by the formula (2) is the compound represented by the formula (1): the compound represented by the formula (2)=1:0.8 to 1:1.5, with 1:1 being preferable.

The contact of the compound represented by the formula (1) and the compound represented by the formula (2) may be conducted in an organic solvent, for example. As the organic solvent, tetrahydrofuran, diethyl ether, 1,4-dioxane or the like can be given.

It is not required to isolate the reaction product of the compound represented by the formula (1) and the compound represented by the formula (2).

When the isolation is conducted, it is preferred that the isolation be conducted at a low temperature of about −30° C. However, a specific apparatus which enables the conditions to be kept is required, and hence, not realistic. Therefore, normally, isolation is conducted at room temperature. However, if the reaction product is placed at room temperature, racemization is accelerated, and hence, a highly-pure meso-form double-cross-linked ligand cannot be obtained.

Accordingly, it is preferred that an anionization agent be introduced while retaining the low-temperature conditions (−25° C. or less) without conducting an isolation reaction. Due to the introduction of an anionization agent, recemization is stopped, whereby a highly pure meso-form double-cross-linked ligand is obtained as an anion body.

An anionization agent is introduced within 5 hours after the contact of the compound represented by the formula (1) and the compound represented by the formula (2). By introducing an anionization agent within 5 hours, racemization with the passage of time can be suppressed to minimum, whereby selectivity can be enhanced. The time before the introduction of an anionization agent is preferably short, more preferably 4 hours or less. If the time is too short, the cross-linkage forming reaction may not proceed sufficiently. Therefore, it is preferred that an anionization agent be introduced after a 10-minute or longer reaction after the contact.

The anionization agent is a compound having a function of drawing out a proton of the compound (1) and the compound (2) as mentioned above. Examples of the anionization agent include alkyllithium can be given, for example. Specific examples thereof include normal butyllithium, sec-butyllithium, tert-butyllithium, and lithium diisopropylamide or the like. In respect of easiness in handling or reactivity, normal butyllithium is preferable.

It suffices that an anionization agent be incorporated in such an amount that the molar ratio of the compound represented by the formula (1) and the anionization agent be: compound represented by the formula (1): anionization agent=1:2 to 1:2.5, preferably compound represented by the formula (1): anionization agent=1:2.2.

Hereinbelow, each substituent represented by the formula (1), the formula (2) and the formula (3) will be explained.

In the formula (1) or (3), as examples of the hydrocarbon group having 1 to 20 carbon atoms, an alkyl group such as a methyl group, an ethyl group, a propyl group, a butyl group, a hexyl group, a cyclohexyl group and an octyl group; an alkenyl group such as a vinyl group, a propenyl group and a cyclohexenyl group; an arylalkyl group such as a benzyl group, a phenylethyl group and a phenylpropyl group; and an aryl group such as a phenyl group, a tolyl group, a dimethylphenyl group, a trimethylphenyl group, an ethylphenyl group, a propylphenyl group, a biphenyl group, a naphthyl group, a methylnaphthyl group, an anthracenyl group and a phenanthryl group.

As the silicon-containing group, a silicon-containing group having 1 to 20 carbon atoms is preferable. Specific examples thereof include a monohydrocarbon-substituted silyl group such as a methylsilyl group and a phenylsilyl group; di-hydrocarbon-substituted silyl group such as a dimethylsilyl group and a diphenylsilyl group; a trihydrocarbon-substituted silyl group such as a trimethylsilyl group, a triethylsilyl group, a tripropylsilyl group, dimethyl(t-butyl)silyl group, a tricyclohexylsilyl group, a triphenylsilyl group, a dimethylphenylsilyl group, a methyldiphenylsilyl group, a tritolylsillyl group, and a trinaphthylsilyl group; a hydrocarbon-substituted silyl ether group such as a trimethylsilyl ether group; a silicon-substituted alkyl group such as a trimethylsilylmethyl group, a bis(trimethylsilyl)methyl group and a phenyldimethylsilylethyl group; a silicon-substituted aryl group such as a trimethylsilylphenyl group or a dimethylhydrosilyl group, a methyldihydrosilyl group or the like can be given. Of these, a silicon-substituted alkyl group is preferable, with a trimethylsilylmethyl group, a phenyldimethylsilylethyl group or the like being particularly preferable.

As the hetero-atom-containing group, a hetero-atom-containing hydrocarbon group or the like can be given. As the hetero-atom-containing hydrocarbon group, a p-fluorophenyl group, a 3,5-difluorophenyl group, a pentachlorophenyl group, a 3,4,5-trifluorophenyl group, a pentafluorophenyl group, a 3,5-bis(trifluoromethyl)phenyl group, a bis(trimethylsilyl)methyl group or the like can be given.

A and A' are independently a cross-linking group containing an atom belonging to the 14$^{th}$ group of the periodic table. As the atom belonging to the 14$^{th}$ group of the periodic table, carbon, silicon, germanium and tin are preferable. As the above-mentioned cross-linking group, a group represented by the following formula can be given, for example.

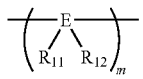

wherein E is carbon, silicon, tin or germanium; $R_{11}$ and $R_{12}$ are independently a hydrogen atom, a hydrocarbon group having 1 to 20 carbon atoms, an alkoxy group having 1 to 20 carbon atoms, an aryloxy group having 6 to 20 carbon atoms or a silicon-containing group having 1 to 20 carbon atoms; they may be the same or different, and may be bonded with each other to form a ring.

m is an integer of 1 to 4, preferably 1 or 2. If m is an integer of 2 or more, plural Es, $R_{11}$s and $R_{12}$s may be the same or different.

$R_{11}$ and $R_{12}$ are preferably a hydrocarbon group having 1 to 6 carbon atoms, more preferably a hydrocarbon group having 1 to 4 carbon atoms, with a methyl group being further preferable.

As examples of the hydrocarbon group having 1 to 20 carbon atoms and the silicon-containing group having 1 to 20 carbon atoms, the same examples as mentioned above can be given.

As examples of the alkoxy group having 1 to 20 carbon atoms and the aryloxy group having 6 to 20 carbon atoms, a methoxy group, an ethoxy group, various propoxy groups, various butoxy groups, various pentoxy groups, various hexoxy groups, various octoxy groups, a phenoxy group, a methylphenoxy group, a naphthoxy group or the like can be given.

The cross-linking group is preferably —Si($R_{13}$)$_2$—. $R_{13}$s are independently a hydrogen atom or a hydrocarbon group having 1 to 20 carbon atoms.

Specific examples of A and A' include methylene, ethylene, ethylidene, (tetramethyl)ethylene, isopropyridene, cyclohexylidene, 1,2-cyclohexylene, dimethylsilylene, methylphenylsilylene, diphenylsilylene, tetramethyldisilylene, dimethylgermirene, dimethylstannylene, 1,2-phenylene, vinylene, vinylidene, ethenylidene (CH$_2$=C=) or the like. Of these, methylene (CH$_2$), isopropylidene [(CH$_3$)$_2$C], ethylene (CH$_2$CH$_2$), (tetramethyl)ethylene[(CH$_3$)$_2$CH$_3$)$_2$C], dimethylsilylene [(CH$_3$)$_2$Si], tetramethyldisilylene [(CH$_3$)$_2$Si(CH$_3$)$_2$Si] and diphenylsilylene [(C$_6$H$_5$)$_2$Si] are preferable due to easiness in synthesis or catalyst yield.

It is preferred that A be dimethylsilylene or tetramethyldisilylene and A' be dimethylsilylene or tetramethyldisilylene.

M and M' are an atom belonging to the 1$^{st}$ or the 2$^{nd}$ group of the periodic table. In respect of easiness in handling or reactivity, a lithium atom, a sodium atom and a magnesium atom are preferable.

n is 1 or 2, when the charge of M is +1 (i.e. when M is Li, Na or K, for example), n is 1 and when the charge of M is +2 (i.e. when M is Mg or Ca), n is 2.

In the compound represented by the formula (2), X is a halogen atom. That is, X is a fluorine atom, a chlorine atom, a bromine atom and an iodine atom. In respect of easiness in handling or reactivity, a chlorine atom or a bromine atom is preferable.

In the second production method of the invention, the compounds represented by the formulas (1) and (2) are brought into contact with each other at a temperature of 45° C. or more. After the passage of 1 hour or more from the contact, an anionization agent is incorporated. According to the second production method of the invention, an anionized receme-form double-cross-linked ligand can be obtained in a high yield (90% or more, for example, 100%, preferably).

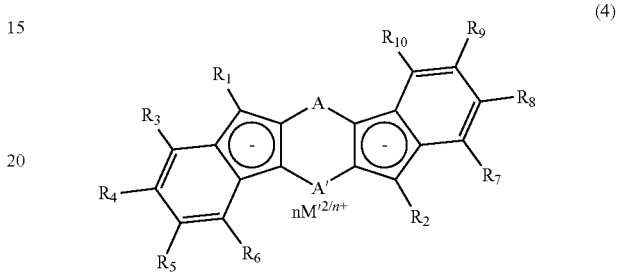

$R_1$ to $R_{10}$, A and n are the same as those mentioned in the formula (1), A' is the same as that mentioned in the formula (2) and M' is the same as that mentioned in the formula (3).

As for the meso-form double-cross-linked ligand obtained by bringing the compound represented by the formula (1) into contact with the compound represented by the formula (2), a raceme reaction proceeds after passing though an energy-consuming reaction such as cutting or recombination of a carbon-silicon bonding, it is racemized by the contact under high-temperature conditions (45° C. or higher), whereby a highly-pure racemic-form double-cross-linked ligand is obtained. Therefore, higher reaction conditions are preferable. The reaction temperature is preferably 50° C. or more, with 60° C. or more being more preferable. If the temperature is too high, the compound represented by the formula (1) may be decomposed. Therefore, the temperature is preferably 100° C. or less.

It is preferred that the temperature be retained at 45° C. or higher from the contact to the incorporation of an anionization agent.

The reaction product of the compound represented by the formula (1) and the compound represented by the formula (2) may or may not be isolated. In respect of work efficiency, it is preferred not to isolate. By omitting an isolation operation, loss of a product by isolation can be eliminated, and the production cost can be suppressed since one step can be omitted.

In order to obtain a highly pure racemic-form double-cross-linked ligand, it is required to fully recemize the meso-form double-cross-linked ligand formed at the early stage of the reaction. Therefore, the time until the incorporation of an anionization agent is more preferably 1.5 hours or more. The temperature conditions at the time of the incorporation of an anionization agent may be either the reaction time kept as it is or low temperature conditions of about −30° C.

The mixing ratio of the compound represented by the formula (1) and the compound represented by the formula (2) and the organic solvent used for bringing the compound represented by the formula (1) into contact with the compound represented by the formula (2) are the same as those in the 1$^{st}$ production method.

The usable anionization agent or the amount thereof is the same as those in the 1$^{st}$ production method.

By allowing the above-mentioned double-cross-linked ligand (3) or (4) to react with a compound represented by the formula $ZY_{p+2}$ (wherein Z is an atom belonging to the 3$^{rd}$ to the 10$^{th}$ group of the periodic table or a lanthanoid-base metal element; Y is an atom of a halogen element, and p+2 is an atomic value of Z), a meso-form double-cross-linked metallocene complex (5) or a racemic-form double-cross-linked metallocene complex (6) is respectively obtained.

Since a highly-pure double-cross-linked ligand (3) or (4) is used, it is possible to obtain a highly-pure (for example, purity of 90% or more, preferably 100%) double-cross-linked metallocene complex.

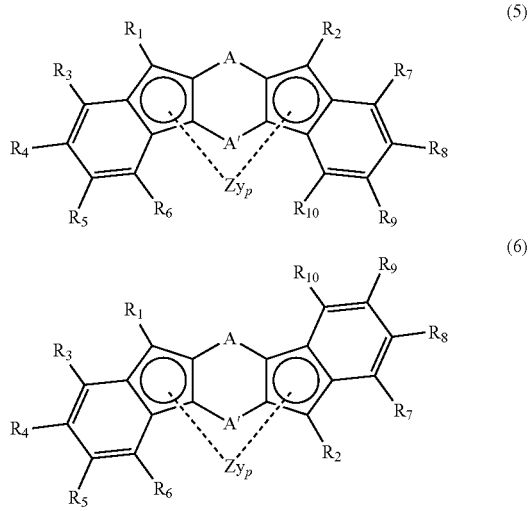

wherein $R_1$ to $R_{10}$, A and A' are independently the same as those in the formula (3) and the formula (4); and Z, Y and p are as mentioned above.

Specific examples of Z include titanium, zirconium, hafnium, yttrium, vanadium, chromium, manganese, nickel, cobalt, palladium and a lanthanoid-based metal. Of these, titanium, zirconium and hafnium which belong to the 4$^{th}$ table are preferable.

As Y, a chlorine atom is preferable.

As the compound represented by $ZY_{p+2}$, zirconium tetrachloride can be given, for example.

EXAMPLES

In each Example and Comparative Example, the production ratio of the meso form and the racemic-form was calculated by a method in which the $^1$HNMR of the product was measured, and the ratio was calculated from each integrated value. The results are shown in Tables 1 and 2.

Production Example 1

Synthesis of a Li salt of 2,2'-diindenyldimethylsilane

In a 200 ml-two-neck flask, THF (10 ml) and Mg (2.5 g, 1.0 mmol) were incorporated. Further, 1,2-dibromoethane (0.1 ml) was added. The resultant was stirred at room temperature for 10 minutes, whereby the Mg surface was activated. To this, 2-bromoindene (5.0 g, 26 mmol) which had been dissolved in THF (40 ml) was added dropwise by means of a pressure equalizing funnel.

The resulting reaction mixture was cooled on ice bath, and then, dichlorodimethylsilane (29.7 ml, 246 mmol) was added dropwise.

After stirring the reaction mixture for overnight, the solvent was distilled off. Extraction was conducted from the resulting solid by using hexane (50 ml×2). By subjecting the resulting extraction solution to evaporation dryness, 2,2'-diindenyldimethylsilane was obtained as a pale yellow oily product (3.47 g, 12.0 mmol, 94%).

The resulting 2,2'-diindenyldimethylsilane was dissolved in diethyl ether (40 ml) and cooled to 0° C. (ice bath). Thereafter, an n-BuLi hexane solution (2.6 M, 9.5 ml, 25 mmol) was added dropwise, and the reaction mixture was stirred for 3 hours at room temperature. Thereafter, the supernatant of the reaction mixture was removed, and the residue (white powder) was washed with hexane (40 ml×2) to obtain white powdery product, whereby an Li salt of 2,2'-diindenyldimethylsilane (Ind-SiMe$_2$-Ind) having the following structure was obtained (3.54 g, 9.45 mmol, 79%, one equivalent ether adduct).

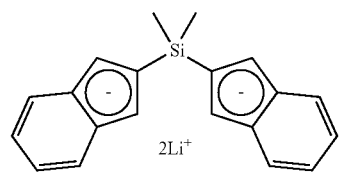

Production Example 2

Synthesis of an Li salt of 2,2'-diindenyltetramethyldisilane

In a 2 L-three-neck flask, THF (300 ml) and Mg (25 g, 1042 mmol) were incorporated. Further, 1,2-dibromoethane (0.1 ml) was added. The resultant was stirred at room temperature for 10 minutes, whereby the Mg surface was activated. To this, 2-bromoindene (100 g, 513 mmol) which had been dissolved in THF (500 ml) was added dropwise by means of a pressure equalizing funnel. After cooling the resulting reaction mixture on ice bath, 1,2-dichlorotetramethyldisilane (46.8 ml, 251 mmol) was added dropwise.

After stirring the reaction mixture for overnight, the solvent was distilled off. Extraction was conducted from the resulting solid by using hexane (500 ml×2). By subjecting the resulting extraction solution to evaporation dryness, 2,2'-diindenyltetramethyldisilane was obtained as a pale yellow product (82 g, 236 mmol, 92%).

The resulting 2,2'-diindenyltetramethyldisilane was dissolved in diethyl ether (500 ml) and cooled to 0° C. (ice bath). Thereafter, an n-BuLi hexane solution (2.6 M, 190 ml, 496 mmol) was added dropwise, and the reaction mixture was stirred for 3 hours at room temperature. Thereafter, the supernatant of the reaction mixture was removed, and the residue (white powder) was washed with hexane (400 ml×2) to obtain white powdery product, whereby an Li salt of 2,2'-diindenyltetramethyldisilane (Ind-SiMe$_2$SiMe$_2$-Ind) having the following structure was obtained (71 g, 192 mmol, 81%, 0.2 equivalent ether adduct).

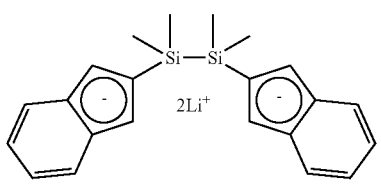

Example 1

(1) An Li salt (0.50 g, 1.3 mmol) of Ind-SiMe$_2$-Ind obtained in Production Example 1 was dissolved in THF (40 ml). The resulting solution was cooled to −30° C., and dichlorodimethylsilane (0.16 ml, 1.3 mmol) was added dropwise. Thereafter, the reaction mixture was stirred at −30° C. for 240 minutes. Then, n-BuLi (2.6 M, 1.1 ml, 2.8 mmol) was added dropwise at that temperature.

The resulting reaction mixture was evaporated to dryness and washed by hexane (20 ml×2), whereby 2Li$^+$ [(1,1'-SiMe$_2$)(2,2'-SiMe$_2$)Ind$_2$]$^{2-}$ was obtained as white powder (0.55 g, 1.3 mmol, 99%) [meso form: racemic-form=95:5]. The structure of the meso form is shown below.

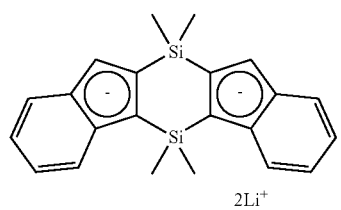

(2) The resulting 2Li$^+$[(1,1-SiMe$_2$)(2,2'-SiMe$_2$)Ind$_2$]$^{2-}$ was suspended in toluene (10 ml). The resultant was cooled to 0° C. A toluene suspension (10 ml) of zirconium tetrachloride (0.31 g, 1.3 mmol) was added dropwise, and the resultant was stirred at room temperature for 2 hours. Thereafter, a supernatant was removed and the residue was extracted with toluene (80 ml). The supernatant and the extracted solution were evaporated to dryness, whereby (1,1'-SiMe$_2$)(2,2'-SiMe$_2$)Ind$_2$ZrCl$_2$ was obtained as a yellow solid (0.36 g, 55%) [meso form: racemic-form=96:4]. The structure of the meso form is shown below.

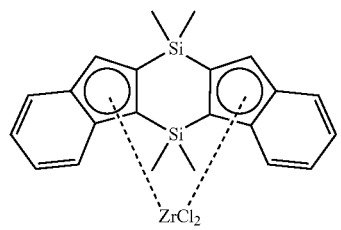

Example 2

(1) An Li salt (0.500 g, 1.33 mmol) of Ind-SiMe$_2$-Ind obtained in Production Example 1 was dissolved in THF (10 ml). The resulting solution was cooled to −30° C., and dichlorotetramethyldisilane (0.25 ml, 1.33 mmol) was added dropwise. Thereafter, the reaction mixture was stirred at −30° C. for 240 minutes. Then, n-BuLi (2.6 M, 1.1 ml, 2.8 mmol) was added dropwise at that temperature.

The resulting reaction mixture was evaporated to dryness and washed by hexane (20 ml×2), whereby 2Li$^+$ [(1,1'-SiMe$_2$SiMe$_2$)(2,2'-SiMe$_2$)Ind$_2$]$^{2-}$ was obtained as white powder (0.660 g, 1.32 mmol, 99%) [meso form: racemic-form=93:7]. The structure of the meso form is shown below.

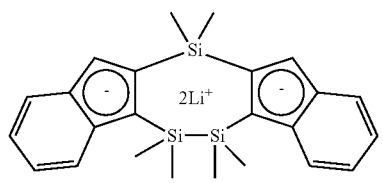

(2) The resulting 2Li$^+$[(1,1-SiMe$_2$SiMe$_2$)(2,2'-SiMe$_2$)Ind$_2$]$^{2-}$ was suspended in toluene (10 ml). The resultant was cooled to 0° C. (ice bath). A toluene suspension (10 ml) of zirconium tetrachloride (0.31 g, 1.3 mmol) was added dropwise, and the resultant was stirred at room temperature for 2 hours. Thereafter, a supernatant was removed and the residue was extracted with toluene (80 ml). The supernatant and the extracted solution were evaporated to dryness, whereby (1,1'-SiMe$_2$SiMe$_2$)(2,2'-SiMe$_2$)Ind$_2$ZrCl$_2$ was obtained as a yellow solid (0.65 g, 83%) [meso form: racemic-form=92:8]. The structure of the meso form is shown below.

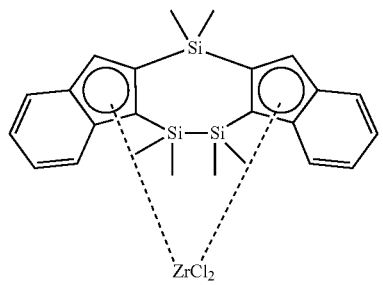

Example 3

An Li salt (2.0 g, 5.4 mmol) of Ind-SiMe$_2$SiMe$_2$-Ind obtained in Production Example 2 was dissolved in THF (30 ml). The resulting solution was cooled to −30° C., and dichlorodimethylsilane (0.71 ml, 5.9 mmol) was added dropwise. Thereafter, the reaction mixture was stirred at −30° C. for 240 minutes. Then, n-BuLi (2.6 M, 4.5 ml, 12 mmol) was added dropwise at that temperature.

The resulting reaction mixture was evaporated to dryness and washed by hexane (20 ml×2), whereby 2Li$^+$[(1,1'-SiMe$_2$)(2,2'-SiMe$_2$SiMe$_2$)Ind$_2$]$^{2-}$ was obtained as white powder (4.0 g, 5.1 mmol, 95%) [meso form: racemic-form=93:7]. The structure of the meso form is shown below.

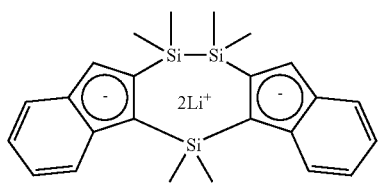

(2) The resulting 2Li⁺[(1,1-SiMe₂)(2,2'-SiMe₂SiMe₂)Ind₂]²⁻ was suspended in toluene (30 ml). The resultant was cooled to 0° C. (ice bath). A toluene suspension (20 ml) of zirconium tetrachloride (1.3 g, 5.4 mmol) was added dropwise, and the resultant was stirred at room temperature for 2 hours. Thereafter, a supernatant was removed and the residue was extracted with toluene (80 ml). The supernatant and the extracted solution were evaporated to dryness, whereby (1,1'-SiMe₂)(2,2'-SiMe₂SiMe₂)Ind₂ZrCl₂ was obtained as a yellow solid (2.2 g, 78%) [meso form: racemic-form=96:4]. The structure of the meso form is shown below.

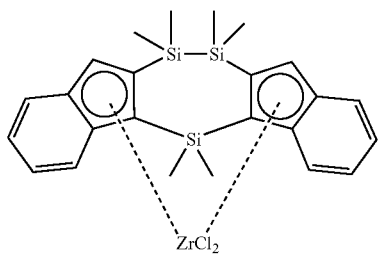

Example 4

(1) An Li salt (0.500 g, 1.33 mmol) of Ind-SiMe₂SiMe₂-Ind obtained in Production Example 2 was dissolved in THF (10 nil). The resulting solution was cooled to −30° C., and dichlorotetramethyldisilane (0.25 ml, 1.33 mmol) was added dropwise. Thereafter, the reaction mixture was stirred at −30° C. for 240 minutes. Then, n-BuLi (2.6 M, 1.1 ml, 2.8 mmol) was added dropwise at that temperature.

The resulting reaction mixture was evaporated to dryness and washed by hexane (20 ml×2), whereby 2Li⁺ [(1,1'-SiMe₂SiMe₂)(2,2'-SiMe₂SiMe₂)Ind₂]²⁻ was obtained as white powder (0.71 g, 1.3 mmol, 98%) [meso form: racemic-form=95:5]. The structure of the meso form is shown below.

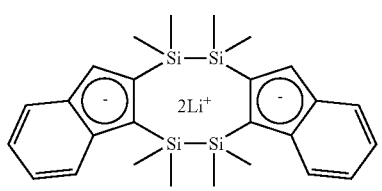

(2) The resulting 2Li⁺ [(1,1'-SiMe₂SiMe₂)(2,2'-SiMe₂)Ind₂]²⁻ was suspended in toluene (10 ml). The resultant was cooled to 0° C. (ice bath). A toluene suspension (10 ml) of zirconium tetrachloride (0.31 g, 1.3 mmol) was added dropwise, and the resultant was stirred at room temperature for 2 hours. Thereafter, a supernatant was removed and the residue was extracted with toluene (80 ml). The supernatant and the extracted solution were evaporated to dryness, whereby (1,1'-SiMe₂SiMe₂)(2,2'-SiMe₂SiMe₂)Ind₂ZrCl₂ was obtained as a yellow solid (0.69 g, 85%) [meso form: racemic-form=94:6]. The structure of the meso form is shown below.

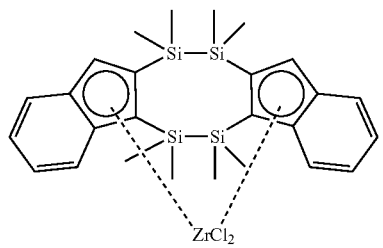

Example 5

A double-cross-linking reaction was conducted in the same manner as in Example 1(1), except that dichlorodimethylsilane was heated to 50° C. before the dropwise addition and the reaction mixture was stirred at 50° C. for 90 minutes, whereby a double-cross-linked racemic-form ligand shown in the following formula (5a) was obtained (yield: 96%). No meso form was contained.

By using the resulting racemic-form double-cross-linked ligand, a racemic-form double-cross-linked metallocene complex shown in the following formula (5b) was obtained (yield: 52%) in the same manner as in Example 1(2). No meso form was contained.

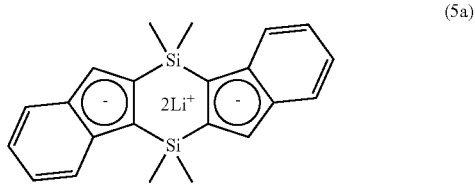

(5a)

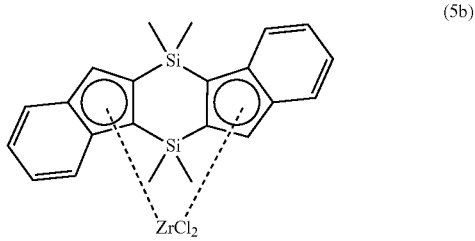

(5b)

Example 6

A double-cross-linking reaction was conducted in the same manner as in Example 4(1), except that dichlorodimethylsilane was heated to 50° C. before the dropwise addition and the reaction mixture was stirred at 50° C. for 90 minutes, whereby a double-cross-linked racemic-form ligand shown in the following formula (6a) was obtained (yield: 98%). No meso form was contained.

By using the resulting racemic-form double-cross-linked ligand, a racemic-form double-cross-linked metallocene complex shown in the following formula (6b) was obtained (yield: 82%) in the same manner as in Example 4(2). No meso form was contained.

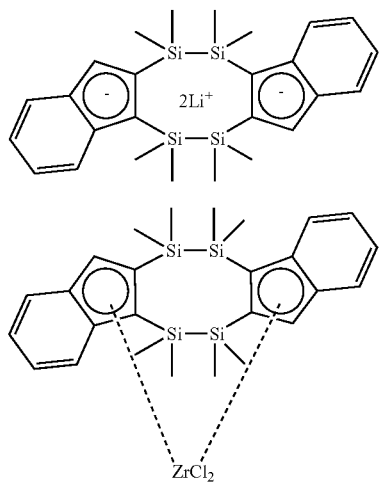

(6a)

(6b)

Comparative Example 1

A double-cross-linked ligand was produced in the same manner as in Example 1(1), except that the double-cross-linking reaction was conducted at −30° C. for 360 minutes in Example 1(1), and a double-cross-linked metallocene complex was obtained in the same manner as in Example 1(2).

Comparative Example 2

A double-cross-linked ligand was produced in the same manner as in Example 1(1), except that the double-cross-linking reaction was conducted at −10° C. for 240 minutes in Example 1(1), and a double-cross-linked metallocene complex was obtained in the same manner as in Example 1(2).

Comparative Example 3

A double-cross-linked ligand was produced in the same manner as in Example 2(1), except that the double-cross-linking reaction was conducted at −30° C. for 360 minutes in Example 2(1), and a double-cross-linked metallocene complex was obtained in the same manner as in Example 2(2).

Comparative Example 4

A double-cross-linked ligand was produced in the same manner as in Example 2(1), except that the double-cross-linking reaction was conducted at −10° C. for 240 minutes in Example 2(1), and a double-cross-linked metallocene complex was obtained in the same manner as in Example 2(2).

Comparative Example 5

A double-cross-linked ligand was produced in the same manner as in Example 3(1), except that the double-cross-linking reaction was conducted at −30° C. for 360 minutes in Example 3(1), and a double-cross-linked metallocene complex was obtained in the same manner as in Example 3(2).

Comparative Example 6

A double-cross-linked ligand was produced in the same manner as in Example 3(1), except that the double-cross-linking reaction was conducted at −10° C. for 240 minutes in Example 3(1), and a double-cross-linked metallocene complex was obtained in the same manner as in Example 3(2).

Comparative Example 7

A double-cross-linked ligand was produced in the same manner as in Example 4(1), except that the double-cross-linking reaction was conducted at −30° C. for 360 minutes in Example 4(1), and a double-cross-linked metallocene complex was obtained in the same manner as in Example 4(2).

Comparative Example 8

A double-cross-linked ligand was produced in the same manner as in Example 4(1), except that the double-cross-linking reaction was conducted at −10° C. for 240 minutes in Example 4(1), and a double-cross-linked metallocene complex was obtained in the same manner as in Example 4(2).

Comparative Example 9

A double-cross-linked ligand was produced in the same manner as in Example 1(1), except that the double-cross-linking reaction was conducted at 50° C. for 30 minutes in Example 1(1), and a double-cross-linked metallocene complex was obtained in the same manner as in Example 1(2).

Comparative Example 10

A double-cross-linked ligand was produced in the same manner as in Example 1(1), except that the double-cross-linking reaction was conducted at 30° C. for 90 minutes in Example 1(1), and a double-cross-linked metallocene complex was obtained in the same manner as in Example 1(2).

Comparative Example 11

A double-cross-linked ligand was produced in the same manner as in Example 4(1), except that the double-cross-linking reaction was conducted at 50° C. for 30 minutes in Example 4(1), and a double-cross-linked metallocene complex was obtained in the same manner as in Example 4(2).

Comparative Example 12

A double-cross-linked ligand was produced in the same manner as in Example 4(1), except that the double-cross-linking reaction was conducted at 30° C. for 90 minutes in Example 4(1), and a double-cross-linked metallocene was obtained in the same manner as in Example 4(2).

TABLE 1

| | | Ex. 1 | Com. Ex. 1 | Com. Ex. 2 | Ex. 2 | Com. Ex. 3 | Com. Ex. 4 |
|---|---|---|---|---|---|---|---|
| Cross-linking structure | A | | $SiMe_2$ | $SiMe_2$ | | $SiMe_2$ | |
| | A' | | $SiMe_2$ | $SiMe_2$ | | $Me_2SiSiMe_2$ | |
| Double-cross-linking reaction temperature (° C.) | | −30 | −30 | −10 | −30 | −30 | −10 |
| Double-cross-linked reaction time (min) | | 240 | 360 | 240 | 240 | 360 | 240 |
| Yield of Li salt of double-cross-linked ligand | % | 99 | 97 | 95 | 99 | 95 | 95 |
| Meso/raceme ratio of La salt of double-cross-linked ligand | %/% | 95/5 | 83/17 | 82/18 | 93/7 | 85/15 | 83/17 |

TABLE 1-continued

|  |  |  | | | | | |
|---|---|---|---|---|---|---|---|
| Yield of double-cross-linked metallocene complex | % | 55 | 52 | 50 | 83 | 82 | 80 |
| Meso/raceme ratio of double-cross-linked metallocene complex | %/% | 96/4 | 84/16 | 84/16 | 92/8 | 86/14 | 84/16 |

|  |  | Ex. 3 | Com. Ex. 5 | Com. Ex. 6 | Ex. 4 | Com. Ex. 7 | Com. Ex. 8 |
|---|---|---|---|---|---|---|---|
| Cross-linked structure | A | | $Me_2SiSiMe_2$ | | | $Me_2SiSiMe_2$ | |
|  | A' | | $SiMe_2$ | | | $Me_2SiSiMe_2$ | |
| Double-cross-linking reaction temperature (° C.) | | −30 | −30 | −10 | −30 | −30 | −10 |
| Double-cross-linked reaction time (min) | | 240 | 360 | 240 | 240 | 360 | 240 |
| Yield of La salt of double-cross-linked ligand | % | 95 | 96 | 94 | 98 | 98 | 96 |
| Meso/raceme ratio of La salt of double-cross-linked ligand | %/% | 93/7 | 85/15 | 80/20 | 95/5 | 86/14 | 83/17 |
| Yield of double-cross-linked metallocene complex | % | 78 | 80 | 77 | 85 | 85 | 83 |
| Meso/raceme ratio of double-cross-linked metallocene complex | %/% | 96/4 | 82/18 | 82/18 | 94/6 | 85/15 | 84/16 |

TABLE 2

|  |  | Ex. 5 | Com. Ex. 9 | Com. Ex. 10 | Ex. 6 | Com. Ex. 11 | Com. Ex. 12 |
|---|---|---|---|---|---|---|---|
| Cross-linked structure | A | | $SiMe_2$ | | | $Me_2SiSiMe_2$ | |
|  | A' | | $SiMe_2$ | | | $Me_2SiSiMe_2$ | |
| Double-cross-linking temperature (° C.) | | 50 | 50 | 30 | 50 | 50 | 30 |
| Double-cross-linking time (min) | | 90 | 30 | 90 | 90 | 30 | 90 |
| Yield of Li salt of double-cross-linked ligand | % | 96 | 97 | 98 | 98 | 96 | 96 |
| Meso/raceme ratio of double-cross-linked ligand | %/% | 0/100 | 16/84 | 75/25 | 0/100 | 20/80 | 24/76 |
| Yield of double-cross-linked metallocene complex | % | 52 | 50 | 53 | 82 | 84 | 81 |
| Meso/raceme ratio of double-cross-linked metallocene complex | %/% | 0/100 | 14/86 | 72/28 | 0/100 | 23/77 | 22/78 |

In Tables 1 and 2, the "double-cross-linking reaction temperature, time" means the time and temperature from the contact of the compound represented by the formula (1) and the compound represented by the formula (2) to the anionization. The "yield of Li salt of the double-cross-linked ligand" is a yield for a mono-cross-linked body as a raw material. The "yield of double-cross-linked metallocene complex" is a yield for a double-cross-linked ligand.

INDUSTRIAL APPLICABILITY

The method for producing a meso-form and racemic-form double-cross-linked ligand of the invention can be used for producing a double-cross-linked metallocene complex. The double-cross-linked metallocene complex can be used as a catalyst for polyolefin polymerization.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. A method for producing an anionized meso-form double-cross-linked ligand represented by formula (3):

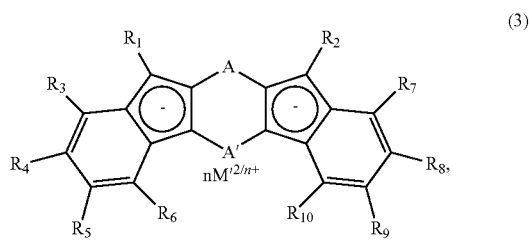

(3)

the method comprising:

contacting a compound represented by formula (1) with a compound represented by formula (2) at −25° C. or less, to form a reaction mixture:

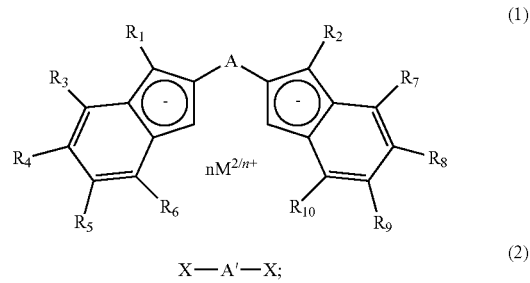

(1)

$$X-A'-X;$$

(2)

and introducing an anionizing agent into the reaction mixture within 5 hours after the contacting, wherein:

$R_1$ to $R_{10}$ independently represent a hydrogen atom, a hydrocarbon group having 1 to 20 carbon atoms, a silicon-containing group or a hetero-atom-containing group;

A and A' independently represent a cross-linking group comprising an atom belonging to the $14^{th}$ group of the periodic table;

M and M' independently represent an atom belonging to the $1^{st}$ or the $2^{nd}$ group of the periodic table;

n represents 2 when M or M' is an atom belonging to the $1^{st}$ group of the periodic table, and represents 1 when M or M' is an atom belonging to the $2^{nd}$ group of the periodic table; and X represents a halogen atom.

2. A method for producing an anionized racemic-form double-cross-linked ligand represented by formula (4):

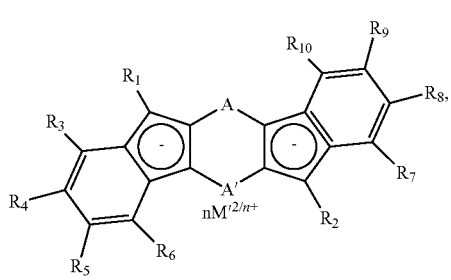

the method comprising:

contacting a compound represented by the formula (1) with a compound represented by the formula (2) at 45° C. or higher, to form a reaction mixture:

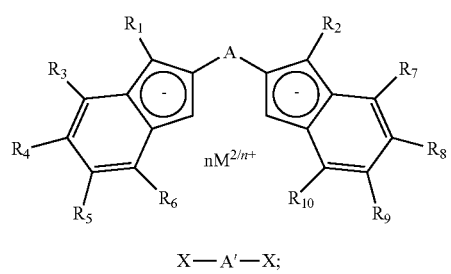

$X-A'-X;$ (2)

and introducing an the anionizing agent into the reaction mixture 1 hour or more after the contacting, wherein:

$R_1$ to $R_{10}$ independently represent a hydrogen atom, a hydrocarbon group having 1 to 20 carbon atoms, a silicon-containing group or a hetero-atom-containing group;

A and A' independently represent a cross-linking group comprising an atom belonging to the $14^{th}$ group of the periodic table;

M and M' independently represent an atom belonging to the $1^{st}$ or the $2^{nd}$ group of the periodic table;

n represents 2 when M or M' is an atom belonging to the $1^{st}$ group of the periodic table, and represents 1 when M or M' is an atom belonging to the $2^{nd}$ group of the periodic table; and X represents a halogen atom.

3. The production method according to claim 1, wherein A is dimethyl silylene or tetramethyl disilylene and A' is dimethyl silylene or tetramethyl disilylene.

4. A method for producing a double-cross-linked metallocene complex, the method comprising forming a double-cross-linked metallocene complex from an anionized meso-form double-cross-linked ligand of formula (3) produced by the method of claim 1.

5. The production method according to claim 2, wherein A is dimethyl silylene or tetramethyl disilylene and A' is dimethyl silylene or tetramethyl disilylene.

6. A method for producing a double-cross-linked metallocene complex, the method comprising forming a double-cross-linked metallocene complex from an anionized racemic-form double-cross-linked ligand of formula (4) produced by the method of claim 2.

* * * * *